US00PP21713P2

(12) United States Plant Patent
Westphal

(10) Patent No.: US PP21,713 P2
(45) Date of Patent: Feb. 15, 2011

(54) ***CLEMATIS* PLANT NAMED 'JENMAR'**

(50) Latin Name: *Clematis patens×lanuginosa*
Varietal Denomination: Jenmar

(76) Inventor: Friedrich Westphal, PeinerHof 7, Prisdorf (DE) 25497

( * ) Notice: Subject to any disclaimer, the term of this patent is extended or adjusted under 35 U.S.C. 154(b) by 0 days.

(21) Appl. No.: 12/584,563

(22) Filed: Sep. 8, 2009

(51) Int. Cl.
*A01H 5/00* (2006.01)

(52) U.S. Cl. ..... Plt./228
(58) Field of Classification Search ..... Plt./228
See application file for complete search history.

*Primary Examiner*—Susan B McCormick Ewoldt

(57) ABSTRACT

A new and distinct *Clematis* cultivar named 'Jenmar' is disclosed, characterized by very compact plant growth and continuous flowering from May through September. Flowers have a distinctive undulating margin. Additionally, the plant has not been observed to produce any seed, and is considered sterile. The new cultivar is a *Clematis,* suitable for ornamental garden purposes.

1 Drawing Sheet

Figure 1:
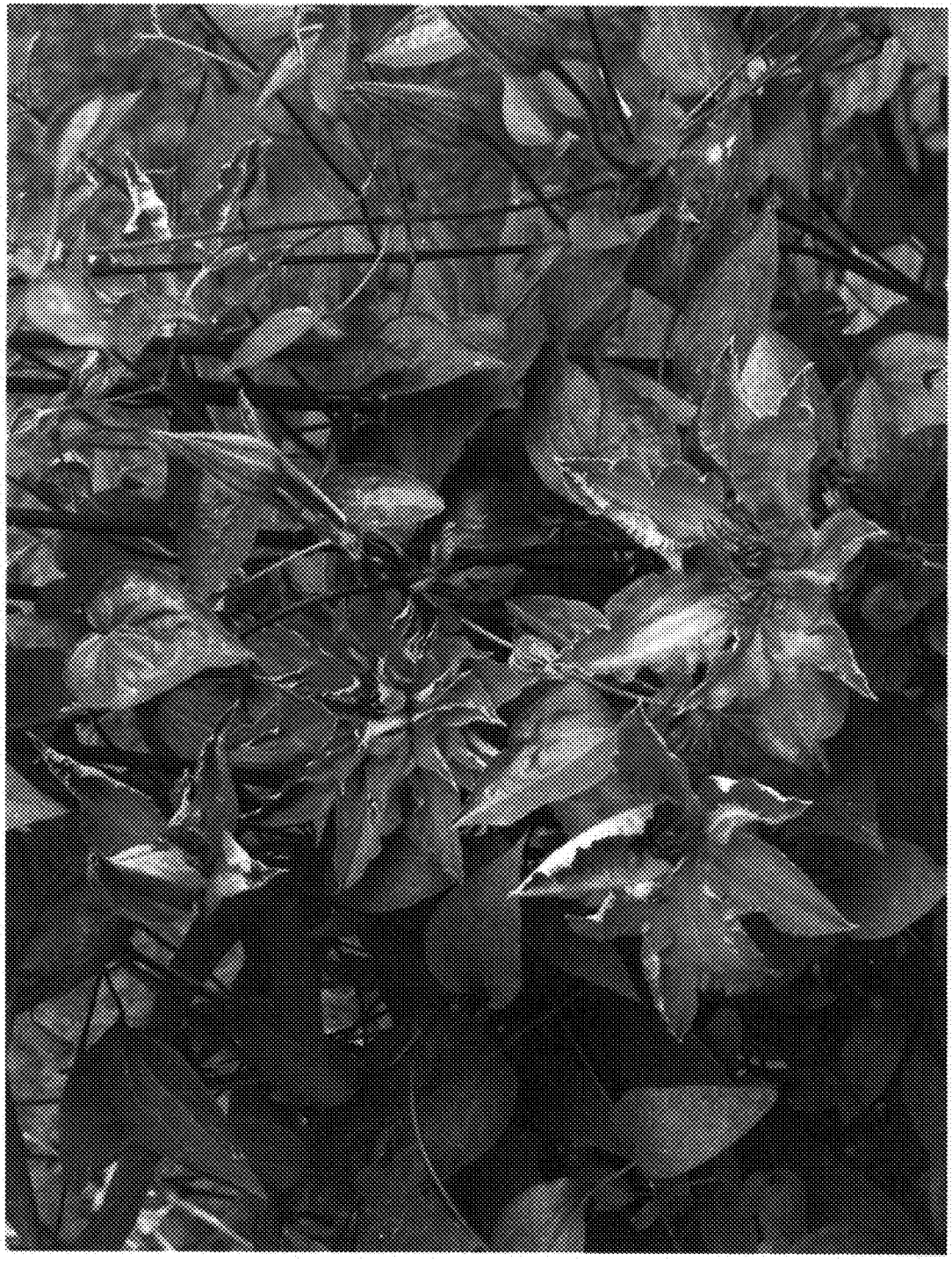

Latin name of the genus and species: *Clematis patens× lanuginosa.*

Variety denomination: 'JENMAR'.

BACKGROUND OF THE INVENTION

The new cultivar is a product of a planned breeding program conducted by the inventor in June 2006. In 2006, the inventor, Friedrich Manfred Westphal organized a group of unnamed, unpatented *Clematis lanuginosa* varieties to open pollinate the seed parent, the unpatented variety *Clematis patens* 'The President.' Seeds originating from this crossing were planted out, and the new variety was selected in late 2007. All work was conducted at a commercial nursery in Pinneberg, Germany.

During 2008 and 2009 the inventor propagated 'Jenmar' by vegetative cuttings at the commercial nursery in Pinneberg, Germany. Subsequent generations have shown that the unique features of this cultivar are stable and reproduced true to type.

SUMMARY OF THE INVENTION

The cultivar 'Jenmar' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Jenmar' These characteristics in combination distinguish 'Jenmar' as a new and distinct *Clematis* cultivar:

1. Very compact plant growth.
2. Continuous flowering from May through September.
3. Sterile flowers.
4. Undulating flower edge.

COMPARISON TO PARENT VARIETY

Plants of the new cultivar 'Jenmar' are similar to plants of the seed parent; *Clematis patens* 'The President' in most horticultural characteristics, however, plants of the new cultivar 'Jenmar' are shorter and more compact. Additionally, plants of 'Jenmar' flower continuously from May through September, whereas 'The President' flowers May and June, stops flowering, then produces another flush of flowers in August or September. Plants of 'The President' produce seed heads, which are not produced by 'Jenmar' due to its sterile flowers.

COMMERCIAL COMPARISON

'Jenmar' can be compared to the well known, unpatented commercial variety 'Elsa Spath.' While 'Jenmar' and 'Elsa Spath' are similar in most horticultural characteristics, as both produce short plants, with a similar flower color, plants of 'Jenmar' differ in having many more tepals. Additionally, plants of 'Jenmar' are overall shorter, by approximately 20 to 30 cm, and flower continuously all Summer, compared to plants of 'Elsa Spath' which consistently stop blooming during the summer, then rebloom during the Fall.

'Jenmar' can also be compared to *Clematis* 'Dorami' filed concurrently with the USPTO, having Ser. No. 12/584,564. The varieties are similar in most horticultural characteristics, however, plants of 'Jenmar' are taller, with many more tepals per flower than 'Dorami.' 'Dorami' typically produces flowers with 6 to 8 tepals, whereas flowers of 'Jenmar' have 50 to 100 tepals, forming a significantly different appearance to the inflorescence.

BRIEF DESCRIPTION OF THE PHOTOGRAPH

The accompanying photograph in FIG. 1 illustrates in full color a close up of typical foliage and flowers of 'Jenmar' grown outdoors in Germany. The plant is approximately 1 year old, and is planted in the ground. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used.

The following observations and measurements describe 'Jenmar' plants grown in a greenhouse in Pinneberg, Germany. Plants are approximately 1 year old, in a 1 liter nursery container. The greenhouse is unheated and unshaded. Temperatures ranged from 2° C. to 20° C. at night to 5° C. to 35° C. during the day. Measurements and numerical values represent averages of typical plant types.

Botanical classification: *Clematis patens×lanuginosa* 'Jenmar'.

PROPAGATION

Time to rooting:

*Initiation.*—Approximately 18 days in the Summer at approximately 24° C. to 25° C.

*Rooted cuttings production.*—Approximately 65 days in the Summer at approximately 20° C. to 28° C.

Root description: Fine, fibrous.

PLANT

Growth habit: Climbing vine.

Height: Approximately 220 to 250 cm, measured from the soil line of the pot after approximately 1 year.

Plant spread: Approximately 70 cm after approximately 1 year.

Growth rate: Rapid. During active growing season in Spring, approximately 60 cm per month.

Branching characteristics: One main stem, and 1 to 3 lateral branches.

Length of main stem: Approximately 180 cm.

Diameter of main stem: Approximately 0.3 cm.

Main stem color: Near RHS Green 139A with flushing near Violet-Blue 93A.

Main stem texture: Slightly pubescent.

Internode length: Varies from 8 to 20 cm.

Strength: Strong, flexible, semi-woody.

FOLIAGE

Leaf:

*Type.*—Simple.

*Arrangement.*—Opposite.

*Leaves per lateral branch.*—Average 4 to 8.

*Average length.*—Approximately 5 to 8 cm.

*Average width.*—Approximately 3 to 5 cm.

*Shape of blade.*—Obovate.

*Apex.*—Acute.

*Base.*—Hastate.

*Attachment.*—Petioled.

*Margin.*—Entire.

*Texture of top surface.*—Smooth.

*Texture of bottom surface.*—Smooth.

*Leaf internode length.*—Approximately 3 cm.

*Color.*—Young foliage upper side: Near RHS Green 141B. Young foliage under side: Near RHS Yellow-Green 144C. Mature foliage upper side: Near RHS Green 139A. Mature foliage under side: Near RHS Green 143B.

*Venation.*—Type: Pinnate. Venation color upper side: Near RHS Yellow-Green 144D. Venation color under side: Near RHS Yellow-Green 145C.

*Petiole.*—Average Length: Approximately 6 to 8 cm. Color: Near RHS Green 139A. Diameter: Approximately 0.15 cm. Texture: Smooth.

Bloom Period:

*Natural season.*—Continuously May through September.

Inflorescence type and habit: Single, axillary; flowers face mostly outward.

Rate of flower opening: Approximately 16 days from bud to fully opened flower.

Flower longevity on plant: Approximately 7 days, after fully opened. Self-cleaning.

Quantity of flowers: Free, continuous flowering, plants have up to 100 flowers and buds at a given time.

Inflorescence size:

*Diameter.*—Approximately 12 to 14 cm.

*Depth.*—Approximately 2 cm.

Corolla:

*Tepal arrangement.*—Tightly held, slightly overlapping single whorl.

*Quantity.*—Approximately 50 to 100 per flower.

*Size.*—Length: Approximately 6 cm. Width: Approximately 2.5 cm.

*Margin.*—Undulating.

*Apex.*—Acute.

*Base.*—Truncate.

*Texture.*—Smooth, velvety.

Color:

*Tepals.*—When opening: Upper surface: Near RHS Violet N87B. Lower surface: Near RHS Violet 86A.

*Fully opened.*—Upper surface: Near RHS Violet-Blue N89C. Lower surface: Near RHS Violet N88A.

*Ageing.*—Upper Surface: Near RHS Violet N88B with interior closer to N87D. Lower Surface: Near RHS Violet N88C.

Bud:

*Shape.*—Ovate.

*Length.*—Approximately 2 to 4 cm.

*Diameter.*—Approximately 0.75 cm.

*Color.*—Near RHS Green 143C with flushing at tip near Violet 86B.

Pedicels:

*Length.*—Approximately 8 cm.

*Width.*—Approximately 0.25 cm.

*Angle.*—Average 70°.

*Strength.*—Strong, flexible.

*Color.*—Near RHS Yellow-Green 144A with flushing near Violet 86A.

Fragrance: None.

REPRODUCTIVE ORGANS

Stamens:

*Number.*—Approximately 90 to 110 per flower.

*Anther length.*—Approximately 1 cm.

*Anther color.*—Near RHS Purple N79A.

*Anther shape.*—Oblong.

*Pollen quantity.*—Not observed to date.

*Filament length.*—Approximately 1.8 cm.

*Filament aspect.*—Straight.

*Filament color.*—Near RHS Purple N79C.

Pistil:

*Number.*—Approximately 60 to 80 per flower.

*Length.*—Approximately 1 cm.

*Style color.*—Near RHS Purple 79B.

*Style length.*—Approximately 1 cm.
*Stigma.*—Shape: Linear. Color: Near RHS Purple 79B.

OTHER CHARACTERISTICS

Seeds and fruits: Not observed to date.
Disease/pest resistance: Neither resistance nor susceptibility to pathogens and pests common to *Clematis* have been observed.
Temperature tolerance: Tolerates temperatures from approximately −20° C. to 45° C.

What is claimed is:

1. A new and distinct cultivar of *Clematis* plant named 'Jenmar' as herein illustrated and described.

* * * * *